Figure 1:
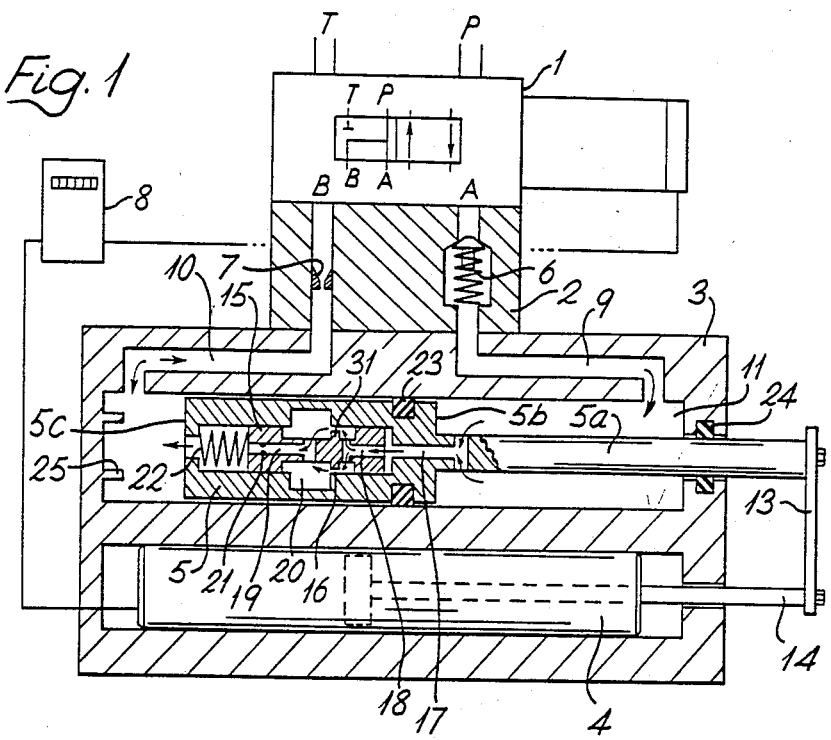

United States Patent [19]

Fisher et al.

[11] Patent Number: 4,663,966
[45] Date of Patent: May 12, 1987

[54] DETERMINING THE LEVEL OF CONTAMINANTS IN A HYDRAULIC SYSTEM

[75] Inventors: Martin J. Fisher, Milton Keynes; Roger A. Heron, Stagsden; Martin L. Hughes, Pagnell, all of England

[73] Assignee: National Research Development Corporation, London, England

[21] Appl. No.: 842,245

[22] Filed: Mar. 21, 1986

Related U.S. Application Data

[63] Continuation of Ser. No. 598,435, Apr. 9, 1984, Pat. No. 4,599,893.

[30] Foreign Application Priority Data

Apr. 18, 1983 [GB] United Kingdom ............... 8310460
Jan. 31, 1984 [GB] United Kingdom ............... 8402434

[51] Int. Cl.⁴ ............................................. G01N 15/06
[52] U.S. Cl. .................................... 73/61 R; 73/61.4
[58] Field of Search ........................ 73/61 R, 53, 61.4

[56] References Cited

U.S. PATENT DOCUMENTS

| | | | |
|---|---|---|---|
| 3,050,987 | 8/1962 | Osgood | 73/61 R |
| 4,468,954 | 9/1984 | Lanctot et al. | 73/61 R |
| 4,495,799 | 1/1985 | Fisher et al. | 73/61 R |
| 4,599,893 | 7/1986 | Fisher et al. | 73/61.4 |

FOREIGN PATENT DOCUMENTS 1098186 1/1968 United Kingdom ............... 73/61 R

Primary Examiner—Stewart J. Levy
Assistant Examiner—Hezron E. Williams
Attorney, Agent, or Firm—Cushman, Darby & Cushman

[57] ABSTRACT

Apparatus and method for determining the level of particulate contamination within the fluid of a hydraulic system. System fluid is introduced through a non-return valve into a space where it is contained by a piston. The structure of the piston includes relatively-movable parts defining a restricted orifice to which fluid, having passed through a drilling in the piston, may escape to drain. When the piston is moved so as to tend to reduce the trapped volume, fluid is expelled from the volume through the drilling and clearance until the clearance becomes blocked by contaminants. The degree of contamination may then be derived from the distance that the piston has moved. The separate parts of piston structure are then relatively-moved to clear the orifice and allow the rest of the trapped fluid to escape, after which the orifice is reset and another volume of fluid introduced to be tested. The piston may be driven by reaction with the system fluid, or alternatively by means independent of that fluid. The specification describes alternative means for measuring the distance travelled by the piston, alternative piston structures to define the orifice, and alternative arrangements of the device as a whole relative to the hydraulic system as a whole.

12 Claims, 4 Drawing Figures

DETERMINING THE LEVEL OF CONTAMINANTS IN A HYDRAULIC SYSTEM

This is a continuation of application Ser. No. 598,435, filed Apr. 9, 1984, and now U.S. Pat. 4,599,893.

This invention relates to determining the level of particulate contamination within a hydraulic system, and an aim of the invention is to provide an effective yet simple apparatus and method making use of a feature that we have found to be characteristic of many hydraulic flow systems in which the typical contaminant particles are of metal or other very hard materials. This feature is that the accumulation of contaminant at a certain type of orifice tends to vary predictably with the volume of hydraulic fluid that has passed through that orifice, assuming a constant degree of contamination of that fluid. Such orifices are sometimes referred to as viscous-loss orifices, and a common example of such an orifice is the radial clearance between a long valve spool and its sleeve. They are of course to be distinguished from orifices with small axial depth and sharp edges, such as are provided by plain holes drilled through thin rigid plates, which tend less to entrap particulate contaminants at all and will be referred to as contaminant-insensitive.

According to one aspect of the invention a device to determine the level of particulate contamination within a hydraulic system comprises an orifice which has access during a period of use to a predetermined volume of hydraulic fluid, a piston arranged in use for free movement from a starting position subject to a predetermined force and associated with the orifice so that the movement of the piston expels fluid from the predetermined volume and ceases when the orifice becomes blocked by contaminants, means within each period of use to record the distance through which the piston has moved from its starting position, and means to reset the device following such recordal by clearing the orifice and returning the piston to its starting position.

One end face of the piston may be exposed in use to fluid at system pressure, and the other end face to a trapped volume of fluid drawn from the system. The two end faces of the piston may be of unequal area, the face exposed to the trapped volume being the smaller of the two, and the orifice may be contained within the body of the piston.

The piston may be so arranged that the flow of the fluid out of the trapped volume through the orifice during use takes place in the direction opposite to that in which the piston moves during use.

The orifice may be defined between the body of the piston and that of a sub-piston mounted for movement within the piston, and the clearance of the orifice may be effected by movement of the sub-piston within the piston.

The device may be located in a hydraulic line arranged in parallel with the main hydraulic system in which the level of particulate contamination is to be determined and include a non-return valve located at the inlet to the parallel hydraulic line to prevent reverse flow of fluid from the line into the main system, the valve being followed by a hydraulic accumulator adapted to maintain substantially constant pressure at the head of the parallel line.

A power source independent of variations of viscosity and other relevant parameters of the system fluid may be used to generate the predetermined force which causes movement of the piston, and the power source may be a gas-filled pressure accumulator.

As yet further alternatives, the orifice may be defined between the piston and a surrounding sleeve, and the space within the device accessible to the hydraulic fluid may be fully enclosed, without the need for rubbing seals.

According to another aspect the invention includes methods of determining particulate contamination using devices as already described, and in particular a method of determining the level of particulate contamination in a main hydraulic circuit in which the circuit fluid is fed also to a parallel sub-circuit containing a piston, in which the piston is caused to move to expel circuit fluid through an orifice formed in the piston from a volume trapped by the piston, in which eventual blockage of the orifice by contaminants prevents further movement of the piston, in which the distance moved by the piston before such blockage is sensed, and in which the degree of contamination of the system fluid is calculated by reference to that distance. The force causing the piston to move may be exerted by the system fluid itself, or by means independent of the system fluid.

Figure 2:
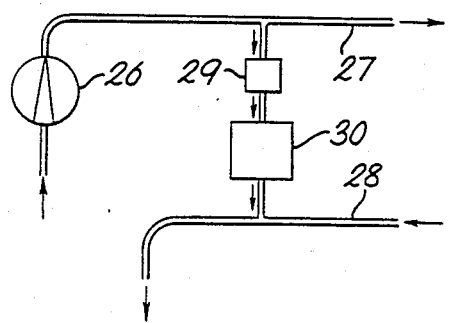
Figure 3:
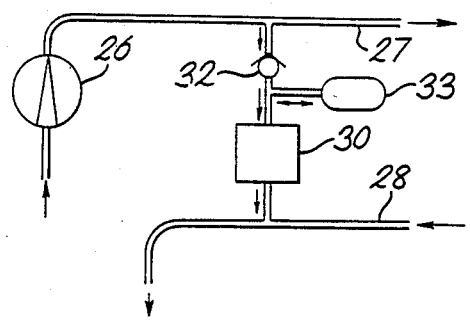
Figure 4:
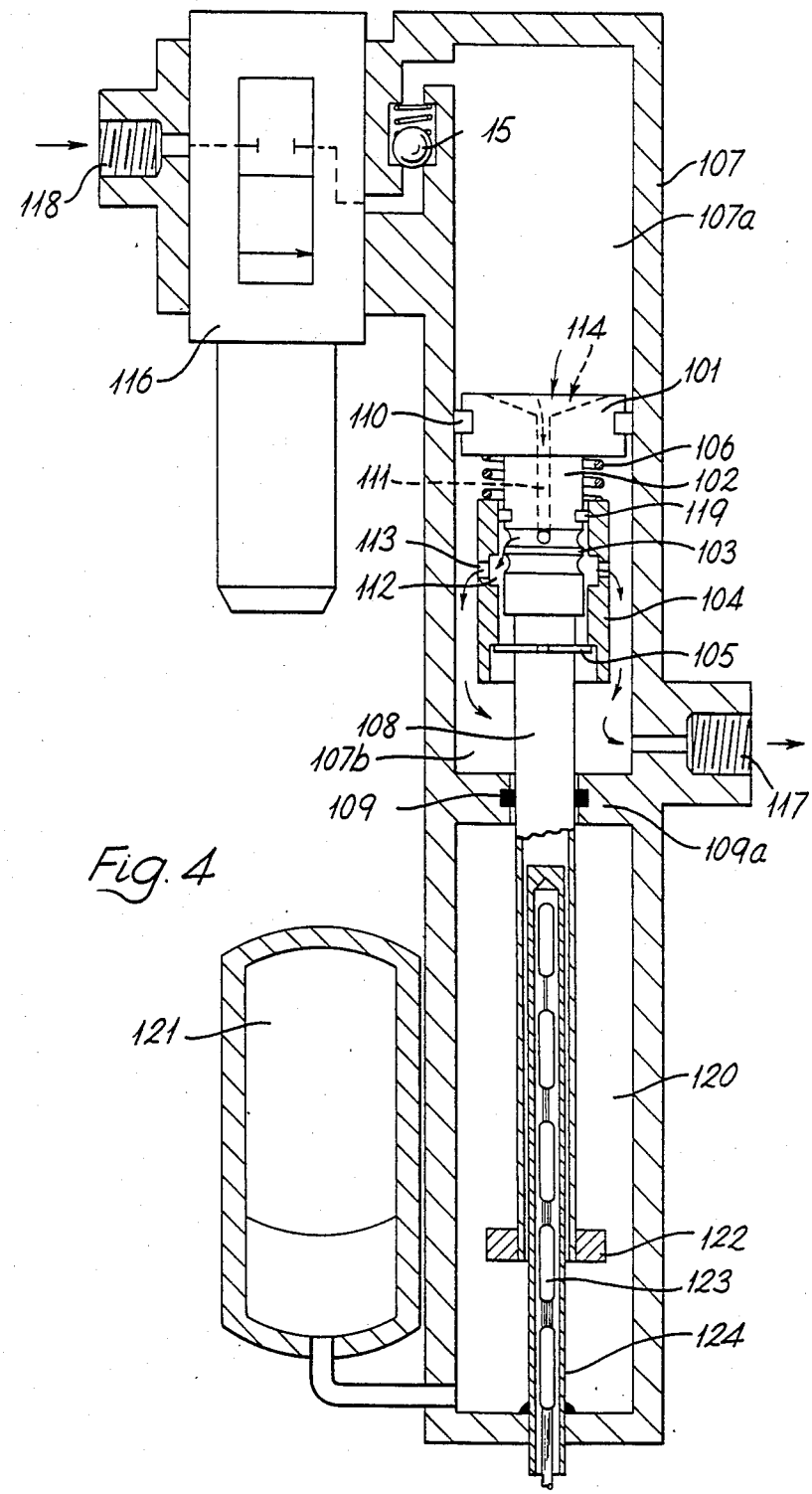

The invention is also defined by the claims and will now be described, by way of example, with reference to the accompanying drawings in which:

FIG. 1 shows some hydraulic components schematically and a piston, sub-piston and associated parts in diagrammatic axial section, FIGS. 2 and 3 are flow diagrams of alternative systems, and FIG. 4 is similar to FIG. 1 but shows an alternative design.

The device comprises a solenoid valve 1, a block 2 including two conduits fitted respectively with a non-return valve 6 and a fixed and contaminant-insensitive restrictor 7, a block 3 containing a piston 5 and a linear voltage differential transformer (LVDT) 4, and a control unit 8.

A drilling 9, formed in block 3, communicates between valve 6 and one end of a bore 11 in which piston 5 moves; a drilling 10 communicates between restrictor 7 and the other end of that bore. Piston 5 is a close fit in bore 11 but free to move along its axis. A link 13 connects the rod 5a of piston 5 with the input shaft 14 of LVDT 4 so that any axial movement of piston 5 is reproduced by the LVDT. A seal 23 prevents leakage of fluid through the clearance between piston 5 and bore 11, and a seal 24 prevents leakage between the bore 11 and the outside of the device.

Piston 5 has a hollow cylindrical interior, within which it carries a close-fitting sub-piston or spool 15, including a land 31 which defines a narrow annular orifice 16 between the spool and the piston. Fluid from the right-hand end of bore 11 may communicate with orifice 16 by way of drillings 17 and 18, and fluid from the left-hand end of bore 11 may communicate with the orifice by way of a drilling 19. Spool 15 is urged towards the right-hand end of its travel by a spring 22, drilling 19 contains a fixed and contaminant-insensitive restrictor 21, a portion 20 of the hollow interior of piston 5 is of increased diameter, and a stop 25 limits leftwards movement of piston 5 in bore 11.

Control unit 8 is electrically connected to solenoid valve 1, and is also electrically connected to LVDT 4 so that when unit 8 operates it records the instantaneous position of the LVDT and thus of piston 5.

The device operates as follows. When solenoid valve 1 is in its non-energised state, fluid at system pressure is connected from inlet P to ports A and B and thence, by way of drillings 9 and 10, to both faces (5b and 5c) of piston 5. Because the area of face 5c is greater than that of face 5b, this ensures that the pressure in the volume of fluid trapped between face 5b and non-return valve 6 will always be higher than the system pressure to which face 5c is exposed by way of port B, restrictor 7 and drilling 10. This inequality of pressures has two consequences: firstly that non-return valve 6 is held firmly shut, and secondly that there is a constant pressure difference which induces fluid to flow from the right-hand side of bore 11 into the left-hand side by way of drillings 17 and 18, orifice 16, drilling 19 and restrictors 21. Spring 22 is rated such that it overcomes the effect of the pressure differences and holds spool 15 to the right-hand end of its travel, and the dimensions of restrictor 21 are such that the pressure drop across that restrictor during this part of the operating cycle device is negligible.

As a result of the movement of fluid through piston 5 from right to left the piston will move to the right, the distance moved being directly proportional to the volume of fluid that has flowed through orifice 16. As that flow takes place, particles of contaminant present in the fluid will become lodged in the orifice and will eventually block it, causing movement of piston 5 then to cease because the fluid to the right-hand side of the piston is trapped with no means to escape. It is known that for certain types of orifice and contaminated fluid, the volume of fluid that can pass through the orifice before the latter becomes blocked bears an ascertainable relationship to the degree of contamination of that fluid. The total movement of piston 5 may thus bear such a relationship to the level of contaminant in the volume of fluid with which the bore and drillings were filled when operation began, and so to the level of contaminants in the system fluid as a whole since that volume was drawn from the system fluid.

At predetermined intervals of time control unit 8 measures the positions of piston 5 by reading the output of LVDT 4, and stores a record of this piston electrically. This record provides a simple means of monitoring the contamination of the fluid. The shorter the distance that piston 5 and LVDT 4 have moved during each interval between recordings of unit 8, the higher the contamination. Each time unit 8 operates, the reading of the position of the LVDT is followed by unit 8 operating to energise valve 1 so that port A is left connected to inlet port P, but port B is connected to port T which is in communication with the return side of the hydraulic system. The pressure of the fluid adjacent the left-hand face 5c of piston 5 therefore falls initially to the pressure at port T, so that the pressure difference operating upon piston 5 is increased and the piston moves to the left-hand end of its travel. During this travel the speed of movement of the piston is controlled by gradual pressure build-up within drilling 10 as fluid passes through the restrictor 7, and since the piston remains "free" the pressure difference across it remains dependent upon the difference in area between faces 5b and 5c. The force on spool 15 is unchanged, and so the spring 22 keeps the spool held at the right-hand end of its travel.

When piston 5 reaches the left-hand end of its travel it meets stop 25. The piston is now no longer "free", and the pressure difference across it rises to approximately the difference between the pressures at ports P and T. The unbalanced force on spool 15 now overcomes spring 22 and the spool moves to the left-hand end of its travel, compressing the spring as it does so. This movement of the spool causes the land 31 to move into register with the portion 20 of the hollow interior of piston 5. Orifice 16 is thus released, and accumulated contaminant falls into the portion 20.

As flow through spool 15 now starts again, a pressure drop develops across restrictor 21 sufficient to maintain adequate force imbalance on spool 15 to hold the spring 22 fully compressed. Fluid now passes from port P through valve 6 and drilling 9 into bore 11, and thence through drillings 17, 18 and 19 and 19 and restrictor 21 to the left-hand side of piston 5, and thence by way of drilling 10 and restrictor 7 to port T. After a period of time adequate to ensure that all fluid in the device is flushed through, control unit 8 de-energises solenoid valve 1, so re-connecting port B to inlet P rather than to port T, and the cycle begins again with a fresh charge of fluid trapped in bore 11 and drilling 9 between piston 5 and non-return valve 6. The sum of the forces exerted by spring 22 and by the fluid at increased pressure to the left-hand side of piston 5 causes spool 15 to return to the right-hand end of its travel.

To ensure optimum reliability and accuracy it is desirable, although not essential, that inlet P should be connected to a supply of system fluid at substantially constant pressure. FIGS. 2 and 3 show alternative means of achieving this. In FIG. 2 a pump 26 supplies pressurised fluid to the main supply line 27 of the hydraulic system. A feed from this line passes through a pressure-regulating valve 29, which feeds fluid at constant pressure to the inlet P of a contaminant monitoring device 30 of the kind shown, for instance, in FIG. 1. The outlet port T of the monitor 30 is connected to the low pressure line 28 of the system. In FIG. 3 pump 26 again feeds fluid at pressure to line 27, and a feed from this line passes now through a non-return valve 32 to the inlet P of monitor 30. A bag-type hydraulic accumulator 33 is also connected to inlet P to maintain pressure substantially constant at this point, and the outlet T of monitor 30 is again connected to the low-pressure hydraulic line 28.

In the alternative design shown in FIG. 4 the piston 101, connected to a piston rod 102, slides within a cylindrical chamber 107. A sleeve 104 is a close fit over a rod 102 but may slide axially over it, and is normally held against a circlip stop 105 by a spring 106. Rod 102 is machined to present a land 103, and there is a carefully dimensioned clearance between this land the sleeve 104. The sleeve 104 is formed with a region 112 of increased bore, and this region is pierced with a number of holes 113 which permit the passage of fluid. A drilling 111 allows fluid to pass axially through the body of piston 101 and rod 102 to reach the clearance at land 103.

The fluid space 107a within chamber 107 and lying to one side of piston 101 is connected by way of an inlet port 118, a non-return valve 115 and a two-port stop valve shown schematically at 116, to the hydraulic system whose contamination is to be determined. The valve 116 may be either manually or electrically actuated. The fluid space 107b on the other side of piston 101 is connected directly by way of a port 117 to the return line or tank of the hydraulic system. Passage of fluid past piston 101, other than by way of drilling 111 and the clearance, is prevented by seals 110 and 119. The entry to drilling 111 is in the form of a shallow cone 114 to encourage any contaminant present in the fluid in space 107a to enter the drilling.

An extension 108 to rod 102 passes through a seal 109 in a wall 109a into a second chamber 120. This chamber is connected to a small "automotive" type bladder accumulator 121. Chamber 120 is filled with hydraulic fluid, and accumulator 121 is filled with a suitable inert gas under pressure and may be fitted with a suitable gas charging valve (not shown) to allow filling and adjustment of gas pressure. Extension 108 carries at its end a magnet 122 which acts to operate a series of reed switches 123 mounted within a blind-ended and hollow rod 124 which is sealed permanently to the casing of chamber 120 and is located with clearance within a drilling in the end of extension 108.

In use the device is preferably mounted with the common axis of rod 102 and extension 108 vertical, and with piston 101 above rod 108. The space 107a above piston 101 has been filled with fluid from the hydraulic system by opening valve 116, allowing fluid to enter the space by way of non-return valve 115, and then shutting valve 116 again. Accumulator 121 is charged with gas to a pressure which, allowing for differential area effects, produces in the trapped fluid within space 107a a pressure a little less than that of the fluid at the point within the hydraulic system to which inlet port 118 is connected. With valve 116 closed, such a pressure forces rod 108 out of chamber 120. The resulting movement of piston 101 within chamber 107 therefore expels fluid from space 107a, down drilling 111 and through the clearance between 103 and 104, and so through holes 113 and port 117 to tank. The clearance becomes progressively blocked by contaminants, and as soon as they completely obstruct it the flow will stop and no further movement of piston 101 up chamber 107 will be possible. The distance moved by piston 101 from its starting position will then be a measure of the level of contamination of the volume of hydraulic fluid originally trapped within space 107a.

To flush the device clear of accumulated contaminants after such an operation and then reset it, valve 116 is first opened to connect system pressure to space 107a. System pressure is of such a value that the downward force exerted upon piston 101 is greater than the upward force due to accumulator 121 so that piston 101 will be forced down the bore of chamber 107 until sleeve 104 meets wall 109a. Further movement of piston 101 compresses spring 106 to bring land 103 into register with the part 112 of sleeve 104, so greatly increasing the clearance between the rod and the sleeve and allowing trapped contaminants to be flushed away through holes 113 and so to tank by way of port 117. Once sufficient time has been allowed for all the contaminants to be flushed away, valve 116 is closed so that the volume of fluid within space 107a is no longer connected to system pressure. The force due to the gas in accumulator 121, assisted by spring 106, therefore moves piston 101 upwards again until it reaches its original level within chamber 107 and until sleeve 104 reaches its original position relative to rod 102. The original clearance is thus re-established between land 103 and the sleeve, and the cycle may begin again.

Any suitable read-out system (not shown) may be associated with reed switches 123 so that the sequential operation of those switches by magnet 122 indicates the position of piston 101, and other reliable sources of motive power unaffected by variations in pressure, viscosity etc. of the fluid within the main hydraulic system can clearly be substituted for the accumulator 121.

We claim:

1. A device to determine the level of particulate contamination within a hydraulic system comprising:
   an orifice, adapted in use to have access to a predetermined volume of the hydraulic fluid of said system;
   piston means having a starting position and arranged in use for movement from that position, and associated with said orifice so that blockage of said orifice by contaminants prevents further said movement of said piston;
   said piston means comprising two parts including portions having there between a clearance and said two parts being capable of relative displacement, said orifice being defined by said clearance;
   means to subject said piston in use to a predetermined force and so cause said movement and expel said fluid from said predetermined volume through said orifice;
   means within a period of use to record the distance through which said piston means moves from said starting position until further movement is prevented as aforesaid, and means to cause said relative displacement between said parts of said piston means and thus clear said orifice, and to return said piston means to said starting position.

2. A device according to claim 1 in which said piston presents opposed first and second end faces, in which said first end face is adapted to be exposed in use to fluid at the pressure of said hydraulic system, and in which said second end face is in communication with said predetermined volume of fluid.

3. A device according to claim 2 in which said first and second end faces of said piston are of unequal area, said second end face being the smaller of the two.

4. A device according to claim 2 in which said orifice is contained within said piston.

5. A device according to claim 4 including a sub-piston mounted for movement within said piston, and in which said orifice is defined between said sub-piston and said piston.

6. A device according to claim 5 in which said sub-piston is adapted to move relative to said piston, whereby said clearance of said orifice is effected by said movement of said sub-piston.

7. A hydraulic system including a device according to claim 1 and including:
   a main hydraulic line in which the said level of particulate contamination is to be determined;
   a subsidiary hydraulic line arranged in parallel with said main hydraulic line, and in which:
   said device is located in said subsidiary hydraulic line.

8. A hydraulic system according to claim 7 including a non-return valve located at the inlet to said parallel subsidiary hydraulic line to prevent reverse flow of fluid from said subsidiary line into said main hydraulic line, and a hydraulic accumulator located in said subsidiary line downstream of said non-return valve and adapted to maintain substantially constant pressure at the head of said subsidiary hydraulic line.

9. A device according to claim 1 including a power source independent of variations of viscosity and other relevant parameters of the said fluid of said hydraulic system, and adapted to generated said predetermined force which causes said movement of said piston.

10. A device according to claim 9 in which said powr source is a gas-filled pressure accumulator.

11. A device according to claim 1 including a sleeve surrounding said piston, and in which said orifice is defined between said piston and said surrounding sleeve.

12. A device according to claim 1 in which the space within said device accessible to said hydraulic fluid is fully enclosed, without the need for rubbing seals.

* * * * *